United States Patent [19]

Wendell

[11] Patent Number: 5,062,836
[45] Date of Patent: Nov. 5, 1991

[54] PLACEMENT DEVICE FOR A CATHETER AND GUIDE WIRE

[75] Inventor: Amy M. Wendell, Franklin, Mass.

[73] Assignee: The Kendall Company, Mansfield, Mass.

[21] Appl. No.: 493,569

[22] Filed: Mar. 14, 1990

[51] Int. Cl.⁵ .............................................. A61M 5/178
[52] U.S. Cl. ..................... 604/167; 604/164; 604/249; 604/263; 604/205; 604/202
[58] Field of Search ................. 604/164–167, 604/201, 202, 205, 240, 242, 243, 249, 263, 264, 168, 169

[56] References Cited

U.S. PATENT DOCUMENTS

| | | | |
|---|---|---|---|
| 3,994,287 | 1/1976 | Turp et al. | 604/167 |
| 4,123,091 | 10/1978 | Cosentino et al. | 604/240 |
| 4,387,879 | 7/1983 | Tauschinski | 604/249 |
| 4,424,833 | 1/1984 | Spector et al. | 606/167 |
| 4,573,978 | 3/1986 | Reilly | 604/240 |
| 4,638,805 | 1/1987 | Powell | 606/192 |
| 4,935,010 | 1/1990 | Cox et al. | 604/167 |

Primary Examiner—C. Fred Rosenbaum
Assistant Examiner—Chalin Smith
Attorney, Agent, or Firm—Alvin Isaacs

[57] ABSTRACT

A placement device for a catheter and guide wire comprising, a valve assembly having a proximal end, a distal end for connection to the catheter, an elastic valve member having a least one slit and a slide member being slidably received in the valve assembly and being movable between a first position spaced from the valve member with the valve member being closed, and a second position engaged against the valve member with the valve member being open, with the slide member having a bore extending therethrough. The device has a valve opener having an elongated stem on an end of the opener with an outer diameter sufficiently small to be received in the bore of the slide member, with the stem having sufficient length to extend through the slide member and open the valve member with the valve opener extending through the valve member, and with the stem having a channel with an inner diameter sufficiently large to receive the guide wire.

6 Claims, 1 Drawing Sheet

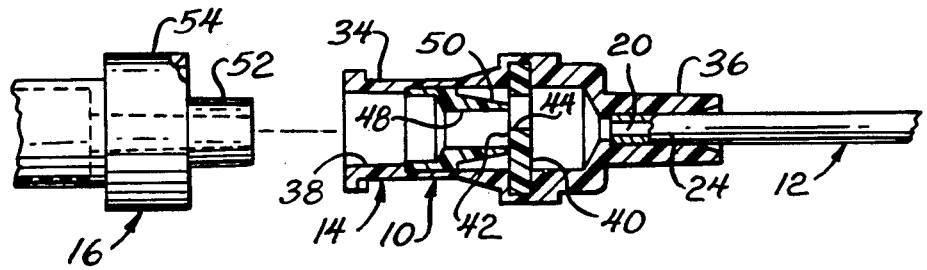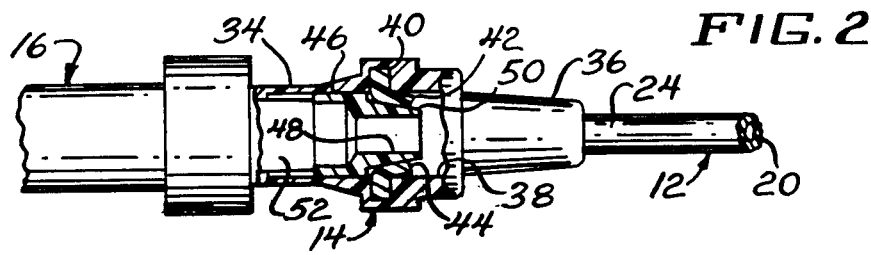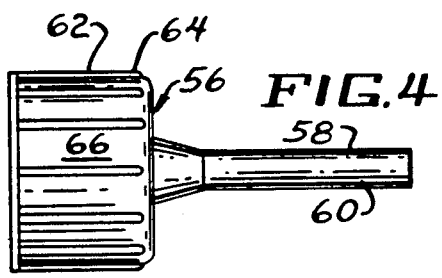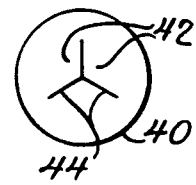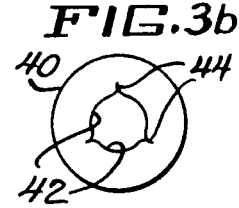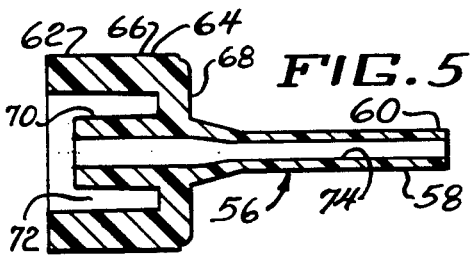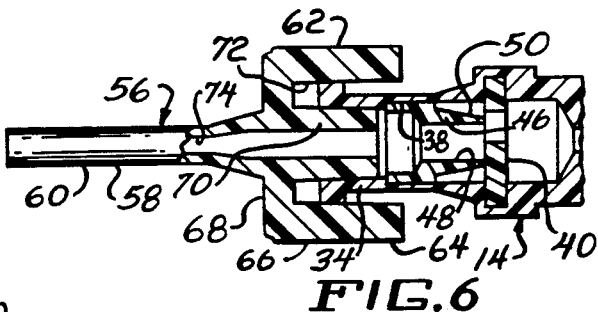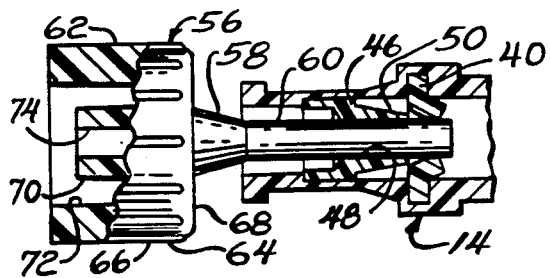

PLACEMENT DEVICE FOR A CATHETER AND GUIDE WIRE

BACKGROUND OF THE INVENTION

The present invention relates to placement devices for a catheter and guide wire.

Before the present invention, the use of central venous pressure (CVP) catheters in conjunction with hemostasis valves have been known. According to the usual procedure, a guide wire is placed in the patient, and the catheter is placed over the guide wire, after which the guide wire is removed from the catheter such that the guide wire facilitates placement of the catheter in the patient. After placement of the catheter, a syringe is utilized in conjunction with the valve which controls the passage of fluid through the catheter.

It has been found relatively difficult to construct a valve which operates in a suitable manner in conjunction with the guide wire. It has been proposed to use a valve having a valve member with a plurality of slits in order to control the passage of fluid therethrough. Further, it has been proposed to utilize a valve assembly retaining the valve member and having a slide member to open and close the valve member response to attachment and removal of the syringe from the valve assembly. However, in this configuration, the valve member obstructs removal of the guide wire through the valve during placement of the catheter and valve assembly.

SUMMARY OF INVENTION

A principal feature of the present invention is the provision of an improved placement device for a catheter and removal of a guide wire.

The placement device of the present invention comprises, a valve assembly having a proximal end, a distal end for connection to the catheter, an elastic valve member having a least one slit and a slide member being slidably received in the valve assembly and being movable between a first position spaced from the valve member with the valve member being closed, and a second position engaged against the valve member with the valve member being open, with the slide member having a bore extending therethrough. The device has a valve opener having an elongated stem on an end of the opener with an outer diameter sufficiently small to be received in the bore of the slide member, and with the stem having sufficient length to extend through the slide member.

A feature of the present invention is that the valve opener opens the valve member after placement through the slide member.

Yet another feature of the invention is that the stem of the valve opener has a channel with an inner diameter sufficiently large to receive the guide wire therethrough.

Thus, a feature of the present invention is that the valve opener may be utilized to actuate and open the valve member and permit removal of the guide wire through the valve opener between the slide member and valve member.

Another feature of the invention is that the valve opener may be releasably attached to the valve assembly prior to use and actuation of the valve member.

Still another feature of the invention is the provision of methods of placing a catheter according to the present invention.

Further features will become more fully apparent in the following description of the embodiments of this invention and from the appended claims.

DESCRIPTION OF THE DRAWINGS

In the drawings:

FIG. 1 is a fragmentary exploded view, taken partly in section, of a placement device of the present invention;

FIG. 2 is a fragmentary sectional view of the placement device of FIG. 1 illustrating a syringe as attached to a valve assembly and a catheter as attached to the valve assembly;

FIG. 3A is a plan view of the valve element of the valve assembly in a closed configuration;

FIG. 3B is a plan view of the valve element of FIG. 3A in an open configuration;

FIG. 4 is an elevational view of a valve opener of the present invention;

FIG. 5 is a sectional view of the valve opener of FIG. 4;

FIG. 6 is a sectional view showing the valve opener releasably attached to a proximal end of the valve assembly with a stem of the valve opener extending away from the valve assembly and the valve element in a closed configuration;

FIG. 7 is a sectional view showing the stem of the valve opener placed in the valve assembly with the valve element in an open configuration; and FIG. 8 is a fragmentary elevational view of a guide wire.

DESCRIPTION OF THE PREFERRED EMBODIMENTS

Referring now to FIG. 1, there is shown a placement device generally designated 10 comprising a catheter or catheter extension generally designated 12, a valve assembly generally designated 14, a syringe generally designated 16, and a guide wire generally designated 18 and illustrated in FIG. 8. With reference to FIGS. 1 and 2, the catheter 12 has a lumen 20 extending therethrough, and a proximal end 24 of the catheter. 12 being solvent bonded to the valve assembly 14. With reference to FIG. 8, the guide wire 18 comprising an elongated wire which may have an resilient straight portion defining a first end 30, and a curved portion adjacent the other end 32.

The valve assembly 14 has a proximal end 34, a distal end 36, and a passageway 38 extending between the proximal and distal ends 34 and 36. As shown in FIG. 2, the catheter 12 is bonded in the passageway 38 of the valve assembly 14 which communicates with the lumen 20 of the catheter 12. With reference to FIGS. 1 and 2, the valve assembly 14 has an elastic valve member 40 secured in the valve assembly 14 with the valve member 40 extending across the passageway 38. The valve member 40 has a plurality of slits 44, and in a preferred form three slits, extending from an apex in order to permit opening of the valve member 40. The valve element 40 is shown in a closed configuration in FIG. 3A, with segments 42 of the valve element 40 defined by the slits being in a closed configuration in order to close the valve element 40. The valve element 40 is shown in an open configuration in FIG. 3B, with the segments 42 spaced away from each other some distance in order to open the valve member 40. The valve assembly 14 also has a slide member 46, as shown in FIGS. 2, 6 and 7, slidably received in the passageway 38 of the valve assembly 14, and having a bore 48 extending therethrough. The slide member 46 is moved between a first position spaced from the valve element 40, as shown in FIG. 1, with the valve element 40 in a closed configuration, and a second position, as shown in FIG. 2, with the slide member 46 engaged against the valve member 40, such that a distal curved, tapered end 50 of the slide member 46 causes movement of the segments 42 of the valve member 40 away from each other in order to open the valve member 40 in the second position of the slide member 46. The valve member 40 biases the slide member 46 between the second position toward the first position due to the elasticity of the valve member 40. Thus, in a normal configuration, the slide member 46 is located at its first position spaced from the valve member 40 with the valve member 40 being closed.

As shown in FIG. 1, the syringe 16 has a tip 52 which is received in the passageway 38 in the proximal end 34 of the valve assembly 14. The syringe 16 has a luer lock 54 which engages the proximal end 34 of the valve assembly 14 or slip and secures the syringe 16 to the valve assembly 14 with the tip 52 received in the passageway 38. In this configuration, the tip 52 engages against the slide member 46 of the valve assembly 14 and moves the slide member 46 between the first to second position, such that the slide member 46 engages against the valve member 40 and opens the valve member 40 to permit passage of fluid therethrough. When the syringe 16 is removed from the valve assembly 14, the valve member 40 biases the slide member 46 to its first position in order to close the valve member 40. When the syringe 16 is attached to the valve assembly 14, communication is established between the syringe 16 and the passageway 38 of the valve assembly 14 and communication is established between the passageway 38 of the valve assembly 14 and the lumen 20 of the catheter 12 when it is attached to the valve assembly 14. The catheter 12 is the type termed a central venous pressure catheter, and the valve assembly 14 is termed a hemostasis valve. The valve assembly 14 thus opens and closes in the event of accidental disconnection in order to prevent passage of air into the patient in this event, or prevent fluids passing from the patient in the event of disconnection.

With reference to FIGS. 4 and 5, in accordance with the present invention, the device has a valve opener generally designated 56. The valve opener 56 has a first end 58 having an elongated stem 60, and a second end 62 having a hollow hub 64 with an annular rim 66, and a shoulder 68 extending between an inner portion of the rim 66 and the stem 60. The valve opener 56 has a stub 70 located inside the rim 66 and defining an annular groove 72 intermediate the rim 66 and stub 70. As shown, the valve opener 56 has a channel 74 extending through the stem 60 and stub 70.

In use, the valve opener 56 is packaged with the valve assembly 14 in the configuration illustrated in FIG. 6, with the proximal end 34 of the valve assembly 14 received in the groove 72 of the valve opener 56 in a configuration with the stub 70 received in the passageway 38 of the valve assembly 14 and the rim 66 located over the proximal end 34 of the valve assembly 14. In this manner, the valve opener 56 is releasably attached to the proximal end 34 of the valve assembly 14.

During use of the device, as illustrated in FIG. 7, the valve opener 56 is removed from the valve assembly 14, and the stem 60 of the valve opener 56 is inserted into the passageway 38 of the valve assembly 14. The outer diameter of the stem 60 is sufficiently small in order to permit placement of the stem 60 through the bore 48 of the slide member 46 and the valve member 40, such that the stem 60 of the valve opener 56 opens the valve member 40 while the slide member 46 remains in the first position spaced from the valve member 40. The channel 74 of the valve opener 56 is sufficiently large to receive the guide wire 18. In this configuration, the guide wire 18 may be passed through the channel 74 of the valve opener, and thus the guide wire 18 may be passed in a simplified manner through the valve member 40 and slide member 46 due to the use of the valve opener 56. Thus, the valve opener 56 is utilized to open the valve member 40 for passage of the guide wire 18 through the valve member 40.

In accordance with the present invention, a method is provided for placing the catheter. First, the guide wire 18 is placed in the patient. The hub 64 of the valve opener 56 is initially attached to the proximal end 34 of the valve member 40, and the valve opener 56 is removed from the valve assembly 14. Next, the stem 60 of the valve opener is inserted through the valve member 40 in order to open the valve member 40. Next, the catheter 12 is placed over the guide wire 18 and the guide wire 18 is passed through the valve opener 56 and valve member 40, after which the guide wire 18 is removed through the valve opener 56 and valve member 40. The valve opener 56 is then removed from the valve member 40. Finally, the syringe may be releasably attached to the proximal end 34 of the valve assembly 14 in order to actuate the slide member 46 and valve member 40.

The foregoing detailed description is given for clearness of understanding only and no unnecessary limitations should be understood therefrom, as modifications will be obvious to those skilled in the art.

What is claimed is:

1. In a placement device for a catheter wherein the catheter is introduced into a patient with the aid of a guide wire, the placement device including a valve assembly having a proximal end for connection to a syringe after the guidewire is removed from the patient, a distal end for connection to the proximal end of the catheter, and an elastic valve member having at least one slit and a slide member being slidably received in the valve assembly and moveable between a first position spaced from the valve member with the valve member being closed, and a second position engaged against the valve member with the valve member being open, with the slide member having a bore extending therethrough;

the improvement comprising a valve opener for opening the valve to permit removal of the guidewire therethrough after introducing the catheter into the patient, the valve opener having opposed distal and proximal ends, a channel extending between the opposed ends and having an inner diameter sufficiently large to receive the guide wire at the distal end of the valve opener and to permit passage of the guide wire through the opener and then out the proximal end thereof, the valve opener having an elongated stem at its distal end, the stem having an outer diameter sufficiently small to be releasably received in the bore of the slide member, the stem having a sufficient length to extend through the slide member to open the valve member whereby to permit removal of the guide wire through the opened valve member, the proximal end of the valve opener having means for releasably securing the valve opener on the proximal end of the valve assembly prior to use in placing the catheter in the patient.

2. The device of claim 1 wherein the valve opener comprises a hub on the proximal end of the valve opener having an annular rim, and a shoulder extending proximally from the rim, with the stem extending distally from the shoulder.

3. The device of claim 2 wherein the valve assembly has a passageway extending from the proximal end of the valve assembly to the valve member, in which the shoulder of the valve opener engages against the proximal end of the valve assembly when the stem is received in the passageway, and in which the valve opener has a hollow stub inside the rim and defining a continuation of the channel from the stem, said rim and stub define an annular groove to receive the proximal end of the valve assembly with the stub received in the passageway, and with the proximal end of a valve opener being releasably received on the valve assembly with the stem extending outwardly from the valve assembly.

4. A method of placing a catheter in a patient comprising the steps of:
   (1) providing a catheter placement device as defined in claim 1;
   (2) placing an elongated guide wire in a patient;
   (3) placing the catheter over the guide wire;
   (4) releasably securing the valve opener to the valve assembly by inserting the elongated stem of the valve opener into the proximal end of the valve assembly to open the valve member of the catheter placement device;
   (5) removing the guide wire through the opened valve member and valve opener; and
   (6) removing the valve opener from the valve member.

5. A method as defined in claim 4 wherein the valve opener is releasably secured to the valve assembly before placing the guide wire in the patient.

6. A method as defined in claim 4 including the step of releasably securing a syringe to the valve assembly while opening the valve member after removing the valve opener from the valve assembly.

* * * * *